(12) United States Patent
Mitrophanous et al.

(10) Patent No.: US 6,818,209 B1
(45) Date of Patent: Nov. 16, 2004

(54) RETROVIRAL DELIVERY SYSTEM

(75) Inventors: Kyriacos A. Mitrophanous, Oxford (GB); Deva Patil, Oxford (GB); Alan J. Kingsman, Oxford (GB); Susan M. Kingsman, Oxford (GB); Fiona M. Ellard, Oxford (GB)

(73) Assignee: Oxford Biomedica (UK) Limited, Oxford (GB)

( * ) Notice: Subject to any disclaimer, the term of this patent is extended or adjusted under 35 U.S.C. 154(b) by 0 days.

(21) Appl. No.: 09/701,014

(22) PCT Filed: May 21, 1999

(86) PCT No.: PCT/GB99/01607

§ 371 (c)(1),
(2), (4) Date: Nov. 22, 2000

(87) PCT Pub. No.: WO99/61639

PCT Pub. Date: Dec. 2, 1999

Related U.S. Application Data

(60) Provisional application No. 60/093,149, filed on Jul. 17, 1998.

(30) Foreign Application Priority Data

May 22, 1998 (GB) .............................. 9811153

(51) Int. Cl.[7] ..................... A61K 48/00; C12N 15/867; C12N 15/63; C12N 15/64
(52) U.S. Cl. .................... 424/93.2; 424/93.1; 424/93.6; 435/320.1; 435/235.1; 435/455; 435/456; 435/457; 435/325; 435/5; 435/6; 435/91.31; 435/91.32; 435/91.4; 435/91.41; 435/91.42; 435/462; 435/463; 435/91.33
(58) Field of Search .......................... 435/320.1, 235.1, 435/455, 456, 457, 325, 366, 5, 6, 91.31, 91.32, 91.33, 91.4, 91.41, 91.42, 462, 463, 69.1, 368, 7.1; 424/93.1, 93.2, 93.6

(56) References Cited

U.S. PATENT DOCUMENTS 6,080,912 A * 6/2000 Bremel et al. ................ 800/23
6,277,633 B1 * 8/2001 Olsen ...................... 435/320.1

FOREIGN PATENT DOCUMENTS

| EP | 0 261 940 | 3/1988 |
|---|---|---|
| WO | WO 92 03537 | 3/1992 |
| WO | WO 92 14829 | 9/1992 |
| WO | WO 93 01833 | 2/1993 |
| WO | WO 93 14188 | 7/1993 |
| WO | WO 94 08022 | 4/1994 |
| WO | WO 95 22617 | 8/1995 |
| WO | WO 96 09400 | 3/1996 |
| WO | WO 98 05759 | 2/1998 |

OTHER PUBLICATIONS

Morimoto et al., PNAS, Mar. 1998, vol. 95, pp. 3152–3156.*
Gaudin et al., Virology, 1992, vol. 187, pp. 627–632.*
Andrew Mountain, Gene Therapy: the first decade, Mar. 2000 (vol. 18).*
W. French Anderson, Human gene therapy, Nature vol. 392, Supp, Apr. 30, 1998.*
Inder M. Verma et al, Gene therapy– promises, problems and prospects, Nature vol. 389, Sep. 18, 1997.*
Eric B. Kmeic, Gene Therapy 240 American Scientist, vol. 87, 1999 May–Jun.*
P. Coulon et al, "An Avirulent Mutant of Rabies Virus is Unable to Infect Motoneurons In Vivo and In Vitro", Journal of Virology, vol. 72, No. 1, Jan. 1998, pp. 273–278, American Society for Microbiology.

* cited by examiner

Primary Examiner—David Guzo
(74) Attorney, Agent, or Firm—Thomas J. Kowalski; Frommer Lawrence & Haug, LLP

(57) ABSTRACT

A retroviral delivery system capable of transducing a target site is described. The retroviral delivery system comprises a first nucleotide sequence coding for at least a part of an envelope protein; and one or more other nucleotide sequences derivable from a retrovirus that ensure transduction of the target site by the retroviral delivery system; wherein the first nucleotide sequence is heterologous with respect to at least one of the other nucleotide sequences; and wherein the first nucleotide sequence codes for at least a part of a rabies G protein or a mutant, variant, derivative or fragment thereof that is capable or recognising the target site.

21 Claims, 6 Drawing Sheets

Figure 4:
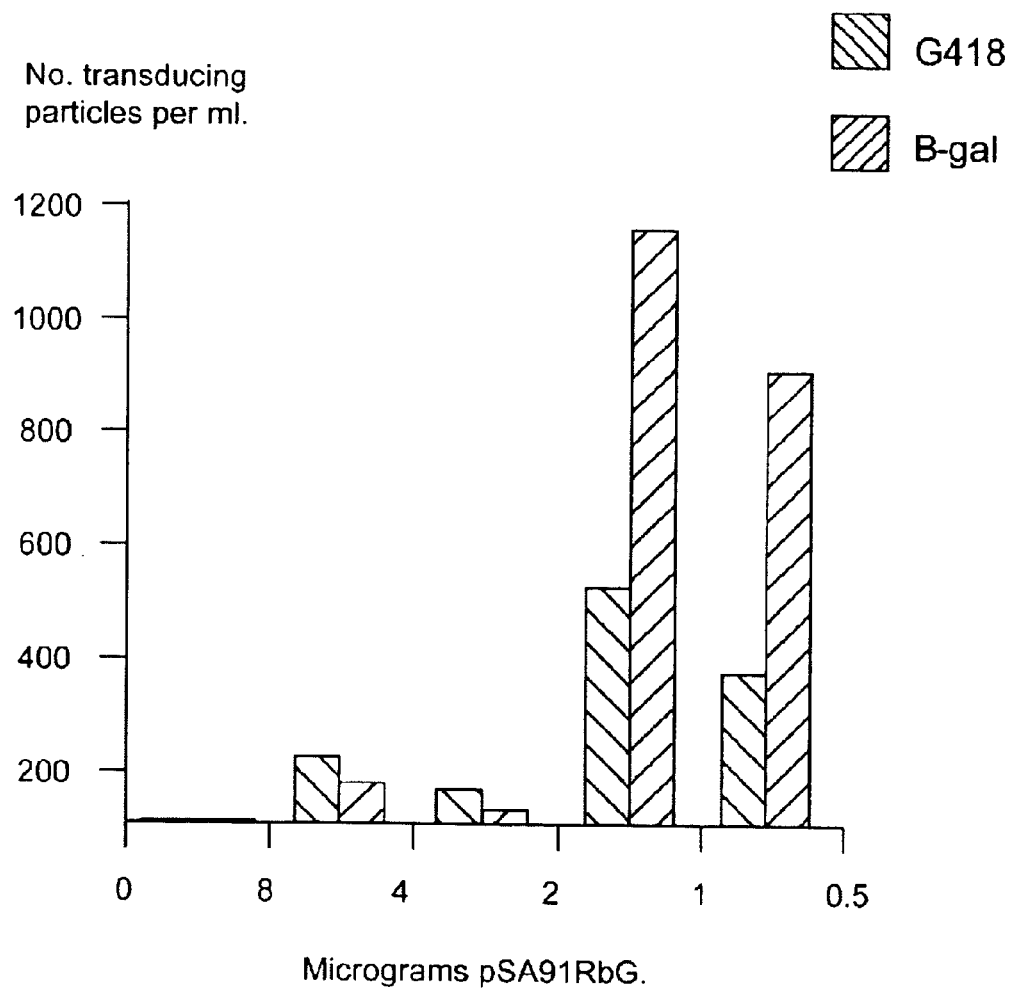

Figure 1 Map of pSA91RbG showing the BglII fragment encoding the rabies G protein cloned into the BamHI site of pSA91.
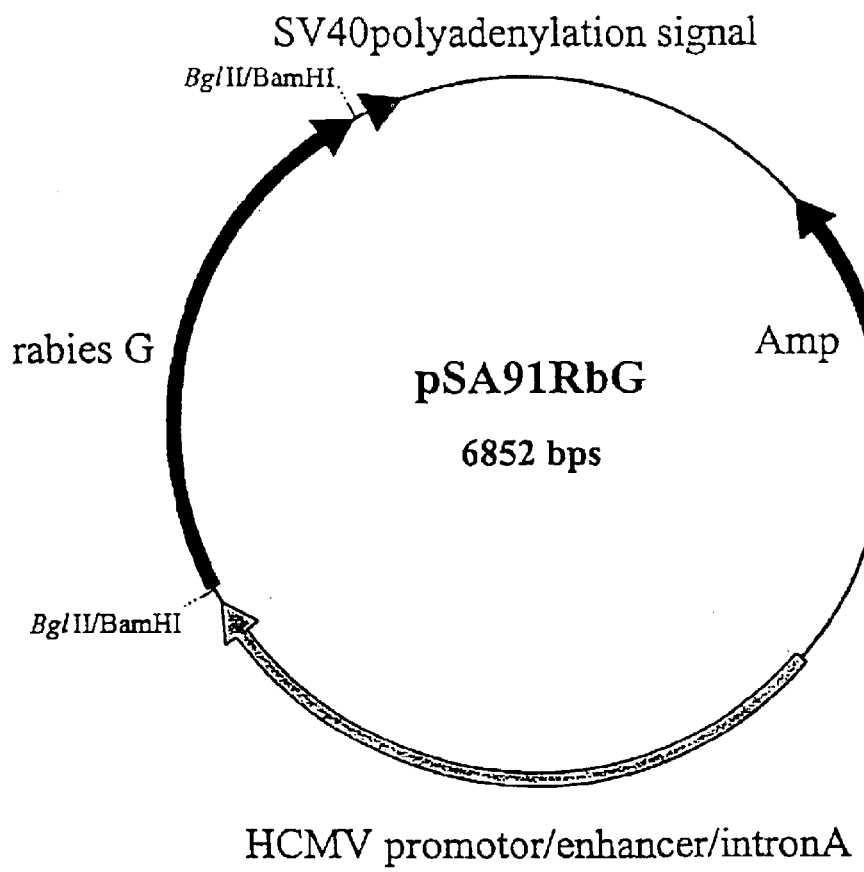

Figure 2    Expression of rabies G protein in 293T cells as confirmed by western blotting.
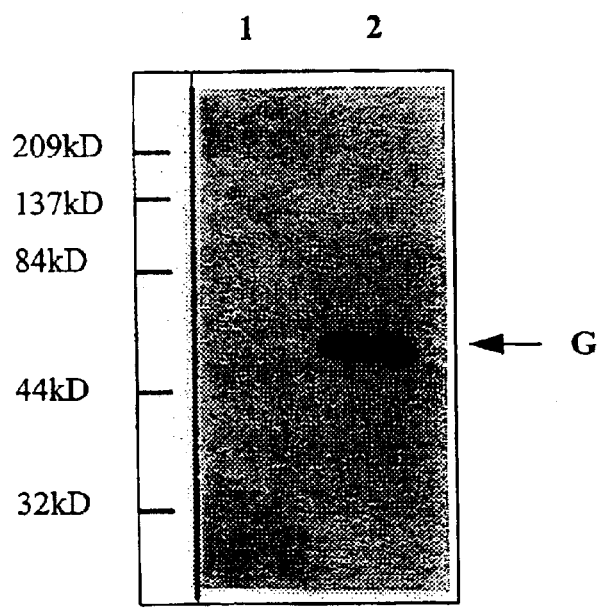
Rabies G protein was detected using a mouse anti-rabies G monoclonal antibody (17D2).
Lane 1.   Cytoplasmic extract from cells transfected with pRV67, pONY2.1nlsLacZ and pONY3.
Lane 2.   Cytoplasmic extract from cells transfected with pSA91RbG, pONY2.1nlsLacZ and pONY3.

Figure 3    Description of vectors used in pseudotyping experiments.
HIV-1 vectors.
pH3Z 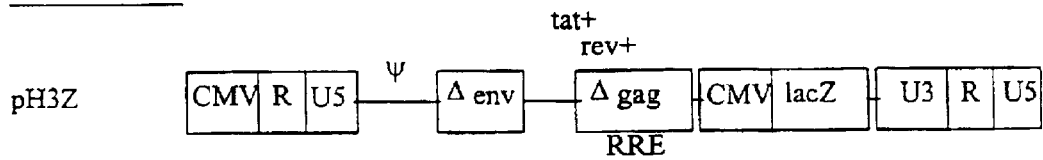
pGp-RRE-1 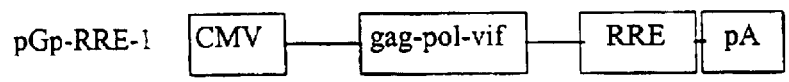
EIAV vectors.
pONY2.1 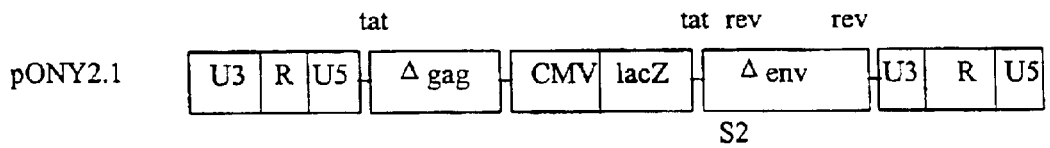
pONY3 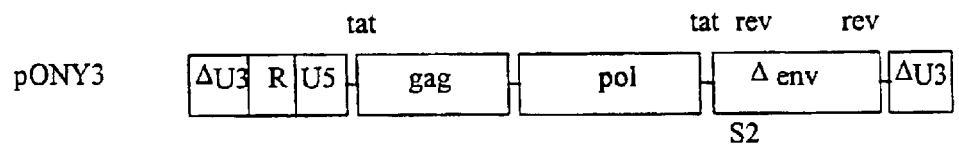
MLV vectors.
pHIT111 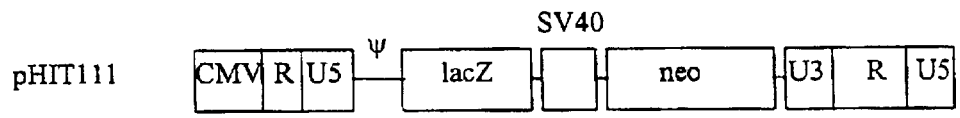
pHIT60 

Optimisation of the yield of MLV particles pseudotyped with rabies G protein by reducing the amount of pSA91RbG used.

FIG. 5

Comparison of the effect of reducing the relative amount of envelope used to produce pseudotyped EIAV particles on the resulting titre.

A. rabies G

No. transducing particles per ml.

Micrograms of pSA91RbG.

B. VSV G

No. transducing particles per ml.

Micrograms pRV67.

SEQUENCE LISTING

```
<160> NUMBER OF SEQ ID NOS: 4

<210> SEQ ID NO 1
<211> LENGTH: 1650
<212> TYPE: DNA
<213> ORGANISM: Artificial Sequence
<220> FEATURE:
<223> OTHER INFORMATION: Description of Artificial Sequence: rabies
      virus strain ERA

<400> SEQUENCE: 1
aggaaagatg gttcctcagg ctctcctgtt tgtacccctt ctggtttttc cattgtgttt     60
tgggaaattc cctatttaca cgatactaga caagcttggt ccctggagcc cgattgacat    120
acatcacctc agctgcccaa acaatttggt agtggaggac gaaggatgca ccaacctgtc    180
agggttctcc tacatggaac ttaaagttgg atacatctta gccataaaaa tgaacgggtt    240
cacttgcaca ggcgttgtga cggaggctga aacctacact aacttcgttg gttatgtcac    300
aaccacgttc aaaagaaagc atttccgccc aacaccagat gcatgtagag ccgcgtacaa    360
ctggaagatg gccggtgacc ccagatatga agagtctcta cacaatccgt accctgacta    420
ccgctggctt cgaactgtaa aaaccaccaa ggagtctctc gttatcatat ctccaagtgt    480
agcagatttg gacccatatg acagatccct tcactcgagg gtcttcccta gcgggaagtg    540
ctcaggagta gcggtgtctt ctacctactg ctccactaac cacgattaca ccatttggat    600
gcccgagaat ccgagactag ggatgtcttg tgacattttt accaatagta gagggaagag    660
agcatccaaa gggagtgaga cttgcggctt tgtagatgaa agaggcctat ataagtcttt    720
aaaaggagca tgcaaactca agttatgtgg agttctagga cttagactta tggatggaac    780
atgggtcgcg atgcaaacat caaatgaaac caaatggtgc cctcccgatc agttggtgaa    840
cctgcacgac tttcgctcag acgaaattga gcaccttgtt gtagaggagt tggtcaggaa    900
gagagaggag tgtctggatg cactagagtc catcatgaca accaagtcag tgagtttcag    960
acgtctcagt catttaagaa aacttgtccc tgggtttgga aaagcatata ccatattcaa   1020
caagaccttg atggaagccg atgctcacta caagtcagtc agaacttgga atgagatcct   1080
cccttcaaaa gggtgtttaa gagttggggg gaggtgtcat cctcatgtga acggggtgtt   1140
tttcaatggt ataatattag gacctgacgg caatgtctta atcccagaga tgcaatcatc   1200
cctcctccag caacatatgg agttgttgga atcctcggtt atcccccttg tgcaccccct   1260
ggcagacccg tctaccgttt tcaaggacgg tgacgaggct gaggattttg ttgaagttca   1320
ccttcccgat gtgcacaatc aggtctcagg agttgacttg ggtctcccga actgggggaa   1380
```

-continued

```
gtatgtatta ctgagtgcag gggccctgac tgccttgatg ttgataattt tcctgatgac    1440
atgttgtaga agagtcaatc gatcagaacc tacgcaacac aatctcagag ggacagggag    1500
ggaggtgtca gtcactcccc aaagcgggaa gatcatatct tcatgggaat cacacaagag    1560
tgggggtgag accagactgt gaggactggc cgtcctttca acgatccaag tcctgaagat    1620
cacctcccct tgggggttc ttttaaaaa                                       1650
```

<210> SEQ ID NO 2
<211> LENGTH: 524
<212> TYPE: PRT
<213> ORGANISM: Artificial Sequence
<220> FEATURE:
<223> OTHER INFORMATION: Description of Artificial Sequence: rabies virus strain ERA

<400> SEQUENCE: 2

Met Val Pro Gln Ala Leu Leu Phe Val Pro Leu Leu Val Phe Pro Leu
1 5 10 15

Cys Phe Gly Lys Phe Pro Ile Tyr Thr Ile Leu Asp Lys Leu Gly Pro
20 25 30

Trp Ser Pro Ile Asp Ile His His Leu Ser Cys Pro Asn Asn Leu Val
35 40 45

Val Glu Asp Glu Gly Cys Thr Asn Leu Ser Gly Phe Ser Tyr Met Glu
50 55 60

Leu Lys Val Gly Tyr Ile Leu Ala Ile Lys Met Asn Gly Phe Thr Cys
65 70 75 80

Thr Gly Val Val Thr Glu Ala Glu Thr Tyr Thr Asn Phe Val Gly Tyr
85 90 95

Val Thr Thr Thr Phe Lys Arg Lys His Phe Arg Pro Thr Pro Asp Ala
100 105 110

Cys Arg Ala Ala Tyr Asn Trp Lys Met Ala Gly Asp Pro Arg Tyr Glu
115 120 125

Glu Ser Leu His Asn Pro Tyr Pro Asp Tyr Arg Trp Leu Arg Thr Val
130 135 140

Lys Thr Thr Lys Glu Ser Leu Val Ile Ile Ser Pro Ser Val Ala Asp
145 150 155 160

Leu Asp Pro Tyr Asp Arg Ser Leu His Ser Arg Val Phe Pro Ser Gly
165 170 175

Lys Cys Ser Gly Val Ala Val Ser Ser Thr Tyr Cys Ser Thr Asn His
180 185 190

Asp Tyr Thr Ile Trp Met Pro Glu Asn Pro Arg Leu Gly Met Ser Cys
195 200 205

Asp Ile Phe Thr Asn Ser Arg Gly Lys Arg Ala Ser Lys Gly Ser Glu
210 215 220

Thr Cys Gly Phe Val Asp Glu Arg Gly Leu Tyr Lys Ser Leu Lys Gly
225 230 235 240

Ala Cys Lys Leu Lys Leu Cys Gly Val Leu Gly Leu Arg Leu Met Asp
245 250 255

Gly Thr Trp Val Ala Met Gln Thr Ser Asn Glu Thr Lys Trp Cys Pro
260 265 270

Pro Asp Gln Leu Val Asn Leu His Asp Phe Arg Ser Asp Glu Ile Glu
275 280 285

His Leu Val Val Glu Glu Leu Val Arg Lys Arg Glu Glu Cys Leu Asp
290 295 300

```
Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
            325                 330                 335

Phe Asn Lys Thr Leu Met Glu Ala Asp Ala His Tyr Lys Ser Val Arg
            340                 345                 350

Thr Trp Asn Glu Ile Leu Pro Ser Lys Gly Cys Leu Arg Val Gly Gly
        355                 360                 365

Arg Cys His Pro His Val Asn Gly Val Phe Phe Asn Gly Ile Ile Leu
        370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
            405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Asn Gln Val Ser Gly
        435                 440                 445

Val Asp Leu Gly Leu Pro Asn Trp Gly Lys Tyr Val Leu Leu Ser Ala
        450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln His Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser His Lys Ser Gly Gly Glu Thr Arg Leu
            515                 520

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 3
gatgctcact acaagtcagt ccagacttgg aatgagatcc tccc                44

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 4
gggaggatct cattccaagt ctggactgac ttgtagtgag catc                44
```

RETROVIRAL DELIVERY SYSTEM

The present application is a U.S. National Phase of PCT/GB99/01607, filed May 21, 1999, which designated the U.S., and claims benefit of U.S. Provisional Application No. 60/093,149, filed Jul. 17, 1998.

The present invention relates to a delivery system. In particular, the present invention relates to a retroviral vector capable of delivering a nucleotide sequence of interest (hereinafter abbreviated to "NOI")—or even a plurality of NOIs—to a site of interest.

More in particular, the present invention relates to a retroviral vector useful in gene therapy.

Gene therapy includes any one or more of: the addition, the replacement, the deletion, the supplementation, the manipulation etc. of one or more nucleotide sequences in, for example, one or more targetted sites—such as targetted cells. If the targetted sites are targetted cells, then the cells may be part of a tissue or an organ. General teachings on gene therapy may be found in Molecular Biology (Ed Robert Meyers, Pub VCH, such as pages 556–558).

By way of further example, gene therapy also provides a means by which any one or more of: a nucleotide sequence, such as a gene, can be applied to replace or supplement a defective gene; a pathogenic gene or gene product can be eliminated; a new gene can be added in order, for example, to create a more favourable phenotype; cells can be manipulated at the molecular level to treat cancer (Schmidt-Wolf and Schmidt-Wolf, 1994, Annals of Hematology 69;273–279) or other conditions—such as immune, cardiovascular, neurological, inflammatory or infectious disorders; antigens can be manipulated and/or introduced to elicit an immune response—such as genetic vaccination.

In recent years, retroviruses have been proposed for use in gene therapy. Essentially, retroviruses are RNA viruses with a life cycle different to that of lytic viruses. In this regard, when a retrovirus infects a cell, its genome is converted to a DNA form. In otherwords, a retrovirus is an infectious entity that replicates through a DNA intermediate. More details on retroviral infection etc. are presented later on.

There are many retroviruses and examples include: murine leukemia virus (MLV), human immunodeficiency virus (HIV), equine infectious anaemia virus (EIAV), mouse mammary tumour virus (MMTV), Rous sarcoma virus (RSV), Fujinarni sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV).

A detailed list of retroviruses may be found in Coffin et al ("Retroviruses" 1997 Cold Spring Harbour Laboratory Press Eds: J M Coffin, S M Hughes, H E Varmus pp 758–763).

Details on the genomic structure of some retroviruses may be found in the art. By way of example, details on HIV may be found from the NCBI Genbank (i.e. Genome Accession No. AF033819).

All retroviruses contain three major coding domains, gag, pol, env, which code for essential virion proteins. Nevertheless, retroviruses may be broadly divided into two categories: namely, "simple" and "complex". These categories are distinguishable by the organisation of their genomes. Simple retroviruses usually carry only this elementary information. In contrast, complex retroviruses also code for additional regulatory proteins derived from multiple spliced messages.

Retroviruses may even be further divided into seven groups. Five of these groups represent retroviruses with oncogenic potential. The remaining two groups are the lentiviruses and the spumaviruses. A review of these retroviruses is presented in "Retroviruses" (1997 Cold Spring Harbour Laboratory Press Eds: J M Coffin, S M Hughes, H E Varmus pp 1–25).

All oncogenic members except the human T-cell leukemia virus-bovine leukemia virus (HTLV-BLV) are simple retroviruses. HTLV, BLV and the lentiviruses and spumaviruses are complex. Some of the best studied oncogenic retroviruses are Rous sarcoma virus (RSV), mouse mammary tumour virus (MMTV) and murine leukemia virus (MLV) and the human T-cell leukemia virus (HTLV).

The lentivirus group can be split even further into "primate" and "non-primate". Examples of primate lentiviruses include the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiencey virus (FIV) and bovine immunodeficiencey virus (BIV).

A critical distinction between the lentivirus family and other types of retroviruses is that lentiviruses have the capability to infect both dividing and non-dividing cells (Lewis et al 1992 EMBO. J 11; 3053–3058, Lewis and Emerman 1994 1. Virol. 68: 510–516). In contrast, other retroviruses—such as MLV—are unable to infect non-dividing cells such as those that make up, for example, muscle, brain, lung and liver tissue.

During the process of infection, a retrovirus initially attaches to a specific cell surface receptor. On entry into the susceptible host cell, the retroviral RNA genome is then copied to DNA by the virally encoded reverse transcriptase which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular proteins. The provirus encodes the proteins and packaging machinery required to make more virus, which can leave the cell by a process sometimes called "budding".

As already indicated, each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral gene. Encapsidation of the retroviral RNAs occurs by virtue of a psi sequence located at the 5' end of the viral genome.

The LTRs themselves are indentical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

Figure 6:
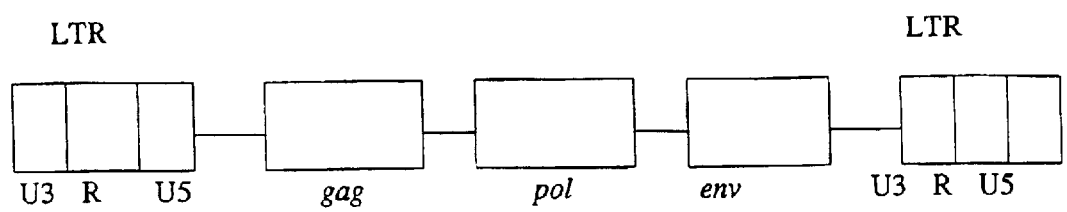

For ease of understanding, a simple, generic diagram (not to scale) of a retroviral genome showing the elementary features of the LTRs, gag, pol and env is presented in FIG. 6.

For the viral genome, the site of transcription initiation is at the boundary between U3 and R in the left hand side LTR (as shown in FIG. 6) and the site of poly (A) addition (termination) is at the boundary between R and US in the right hand side LTR (as shown in FIG. 6). U3 contains most of the transcriptional control elements of the provirus, which include the promoter and multiple enhancer sequences responsive to cellular and in some cases, viral transcriptional activator proteins. Some retroviruses have any one or more of the following genes that code for proteins that are involved in the regulation of gene expression: tat, rev, tax and rex.

With regard to the structural genes gag, pol and env themselves, gag encodes the internal structural protein of the virus. Gag is proteolytically processed into the mature proteins MA (matrix), CA (capsid), NC (nucleocapsid). The gene pol encodes the reverse transcriptase (RT), which contains both DNA polymerase, and associated RNase H activities and integrase (IN), which mediates replication of the genome. The gene env encodes the surface (SU) glycoprotein and the transmembrane (TM) protein of the virion, which form a complex that interacts specifically with cellular receptor proteins. This interaction leads ultimately to fusion of the viral membrane with the cell membrane.

The envelope glycoprotein complex of retroviruses includes two polypeptides: an external, glycosylated hydrophilic polypeptide (SU) and a membrane-spanning protein (TM). Together, these form an oligomeric "knob" or "knobbed spike" on the surface of a virion. Both polypeptides are encoded by the env gene and are synthesised in the form of a polyprotein precursor that is proteolytically cleaved during its transport to the cell surface. Although uncleaved Env proteins are able to bind to the receptor, the cleavage event itself is necessary to activate the fusion potential of the protein, which is necessary for entry of the virus into the host cell. Typically, both SU and TM proteins are glycosylated at multiple sites. However, in some viruses, exemplified by MLV, TM is not glycosylated.

Although the SU and TM proteins are not always required for the assembly of enveloped virion particles as such, they do play an essential role in the entry process. In this regard, the SU domain binds to a receptor molecule—often a specific receptor molecule—on the target cell. It is believed that this binding event activates the membrane fusion-inducing potential of the TM protein after which the viral and cell membranes fuse. In some viruses, notably MLV, a cleavage event—resulting in the removal of a short portion of the cytoplasmic tail of TM—is thought to play a key role in uncovering the full fusion activity of the protein (Brody et al 1994 J. Virol. 68: 4620–4627, Rein et al 1994 J. Virol. 68: 1773–1781). This cytoplasmic "tail", distal to the membrane-spanning segment of TM remains on the internal side of the viral membrane and it varies considerably in length in different retroviruses.

Thus, the specificity of the SU/receptor interaction can define the host range and tissue tropism of a retrovirus. In some cases, this specificity may restrict the transduction potential of a recombinant retroviral vector. For this reason, many gene therapy experiments have used MLV. A particular MLV that has an envelope protein called 4070A is known as an amphotropic virus, and this can also infect human cells because its envelope protein "docks" with a phosphate transport protein that is conserved between man and mouse. This transporter is ubiquitous and so these viruses are capable of infecting many cell types. In some cases however, it may be beneficial, especially from a safety point of view, to specifically target restricted cells. To this end, several groups have engineered a mouse ecotropic retrovirus, which unlike its amphotropic relative normally only infects mouse cells, to specifically infect particular human cells. Replacement of a fragment of an envelope protein with an erythropoietin segement produced a recombinant retrovirus which then bound specifically to human cells that expressed the erythropoietin receptor on their surface, such as red blood cell precursors (Maulik and Patel 1997 "Molecular Biotechnology: Therapeutic Applications and Strategies" 1997. Wiley-Liss linc. pp 45.).

In addition to gag, pol and env, the complex retroviruses also contain "accessory" genes which code for accessory or auxiliary proteins. Accessory or auxiliary proteins are defined as those proteins encoded by the accessory genes in addition to those encoded by the usual replicative or structural genes, gag, pol and env. These accessory proteins are distinct from those involved in the regulation of gene expression, like those encoded by rat, rev, tax and rex. Examples of accessory genes include one or more of vif, vpr, vpx, vpu and nef. These accessory genes can be found in, for example, HIV (see, for example pages 802 and 803 of "Retroviruses" Ed. Coffin et al Pub. CSHL 1997). Non-essential accessory proteins may function in specialised cell types, providing functions that are at least in part duplicative of a function provided by a cellular protein. Typically, the accessory genes are located between pol and env, just downstream from env including the U3 region of the LTR or overlapping portions of the env and each other.

The complex retroviruses have evolved regulatory mechanisms that employ virally encoded transcriptional activators as well as cellular transcriptional factors. These trans-acting viral proteins serve as activators of RNA transcription directed by the LTRs. The transcriptional trans-activators of the lentiviruses are encoded by the viral tat genes. Tat binds to a stable, stem-loop, RNA secondary structure, referred to as TAR, one function of which is to apparently optimally position Tat to trans-activate transcription.

As mentioned earlier, retroviruses have been proposed as a delivery system (other wise expressed as a delivery vehicle or delivery vector) for inter alia the transfer of a NOI, or a plurality of NOIs, to one or more sites of interest. The transfer can occur in vitro, ex vivo, in vivo, or combinations thereof. When used in this fashion, the retroviruses are typically called retroviral vectors or recombinant retroviral vectors. Retroviral vectors have even been exploited to study various aspects of the retrovirus life cycle, including receptor usage, reverse transcription and RNA packaging (reviewed by Miller, 1992 Curr Top Microbiol Immunol 158:1–24).

In a typical recombinant retroviral vector for use in gene therapy, at least part of one or more of the gag, pol and env protein coding regions may be removed from the virus. This makes the retroviral vector replication-defective. The removed portions may even be replaced by a NOI in order to generate a virus capable of integrating its genome into a host genome but wherein the modified viral genome is unable to propagate itself due to a lack of structural proteins. When integrated in the host genome, expression of the NOI occurs—resulting in, for example, a therapeutic effect. Thus, the transfer of a NOI into a site of interest is typically achieved by: integrating the NOI into the recombinant viral vector; packaging the modified viral vector into a virion coat; and allowing transduction of a site of interest—such as a targetted cell or a targetted cell population.

It is possible to propagate and isolate quantities of retroviral vectors (e.g. to prepare suitable titres of the retroviral vector) for subsequent transduction of, for example, a site of interest by using a combination of a packaging or helper cell line and a recombinant vector.

In some instances, propagation and isolation may entail isolation of the retroviral gag, pol and env genes and their separate introduction into a host cell to produce a "packaging cell line". The packaging cell line produces the proteins required for packaging retroviral DNA but it cannot bring about encapsidation due to the lack of a psi region. However, when a recombinant vector carrying a NOI and a psi region is introduced into the packaging cell line, the helper proteins can package the psi-positive recombinant vector to produce the recombinant virus stock. This can be used to infect cells to introduce the NOI into the genome of the cells. The recombinant virus whose genome lacks all genes required to make viral proteins can infect only once and cannot propagate. Hence, the NOI is introduced into the host cell genome without the generation of potentially harmful retrovirus. A summary of the available packaging lines is presented in "Retroviruses" (1997 Cold Spring Harbour Laboratory Press Eds: J M Coffin, S M Hughes, H E Varmus pp 449).

However, this technique can be problematic in the sense that the titre levels are not always at a satisfactory level. Nevertheless, the design of retroviral packaging cell lines has evolved to address the problem of inter alia the spontaneous production of helper virus that was frequently encountered with early designs. As recombination is greatly facilitated by homology, reducing or eliminating homology between the genomes of the vector and the helper has reduced the problem of helper virus production.

More recently, packaging cells have been developed in which the gag, pol and env viral coding regions are carried on separate expression plasmids that are independently transfected into a packaging cell line so that three recombinant events are required for wild type viral production. This strategy is sometimes referred to as the three plasmid transfection method (Soneoka et al 1995 Nucl. Acids Res. 23: 628–633).

Transient transfection can also be used to measure vector production when vectors are being developed. In this regard, transient transfection avoids the longer time required to generate stable vector-producing cell lines and is used if the vector or retroviral packaging components are toxic to cells. Components typically used to generate retroviral vectors include a plasmid encoding the Gag/Pol proteins, a plasmid encoding the Env protein and a plasmid containing, a NOI. Vector production involves transient transfection of one or more of these components into cells containing the other required components. If the vector encodes toxic genes or genes that interfere with the replication of the host cell, such as inhibitors of the cell cycle or genes that induce apotosis, it may be difficult to generate stable vector-producing cell lines, but transient transfection can be used to produce the vector before the cells die. Also, cell lines have been developed using transient infection that produce vector titre levels that are comparable to the levels obtained from stable vector-producing cell lines (Pear et al 1993, PNAS 90:8392–8396).

In view of the toxicity of some HIV proteins—which can make it difficult to generate stable HIV-based packaging cells—HIV vectors are usually made by transient transfection of vector and helper virus. Some workers have even replaced the HIV Env protein with that of vesicular stomatis virus (VSV). Insertion of the Env protein of VSV facilitates vector concentration as HIVIVSV-G vectors with titres of $5 \times 10^5$ ($10^8$ after concentration) were generated by transient transfection (Naldini et al 1996 Science 272: 263–267). Thus, transient transfection of HIV vectors may provide a useful strategy for the generation of high titre vectors (Yee et al 1994 PNAS. 91: 9564–9568). A drawback, however, with this approach is that the VSV-G protein is quite toxic to cells.

Replacement of the env gene with a heterologous ,env gene is an example of a technique or strategy called pseudotyping. Pseudotyping is not a new phenomenon and examples may be found in WO-A-98/05759, WO-A-98/05754, WO-A-97/17457, WO-A-96/09400, WO-A-91/00047 and Mebatsion et al 1997 Cell 90, 841–847.

Pseudotyping can confer one or more advantages. For example, with the lentiviral vectors, the env gene product of the HIV based vectors would restrict these vectors to infecting only cells that express a protein called CD4. But if the env gene in these vectors has been substituted with env sequences from other RNA viruses, then they may have a broader infectious spectrum (Verma and Somia 1997 Nature 389:239–242). As just described—and by way of example—workers have pseudotyped an HIV based vector with the glycoprotein from VSV (Verina and Somia 1997 ibid).

Also, and by way of example, the relative fragility of the retroviral Env protein may limit the ability to concentrate retroviral vectors—and concentrating the virus may result in a poor viral recovery. To some extent, this problem may be overcome by substitution of the retroviral Env protein with the more stable VSV-G protein allowing more efficient vector concentration with better yields (Naldini et al 1996. Science 272: 263–267).

However, pseudotyping with VSV-G protein may not always be desirable. This is because the VSV-G protein is cytotoxic (Chen et al 1996, Proc. Natl. Acad. Sci. 10057 and references cited therein).

Hence, it is desirable to find other proteins which are non-toxic and which can be used to pseudotype a retroviral vector.

Thus, the present invention seeks to provide an improved retroviral vector.

According to a first aspect of the present invention there is provided a retroviral delivery system capable of transducing a target site, wherein the retroviral delivery system comprises a first nucleotide sequence coding for at least a part of an envelope protein; and one or more other nucleotide sequences derivable from a retrovirus that ensure transduction of the target site by the retroviral delivery system; wherein the first nucleotide sequence is heterologous with respect to at least one of the other nucleotide sequences; and wherein the first nucleotide sequence codes for at least a part of a rabies G protein or a mutant, variant, derivative or fragment thereof that is capable of recognising the target site.

The retroviral delivery system of the present invention can comprise one entity. Alternatively, the retroviral delivery system of the present invention can comprise a plurality of entities which in combination provide the retroviral delivery system of the present invention. Examples of these viral delivery systems can include but are not limited to herpesviruses and adenoviruses as described in Savard et al 1997, J Virol 71(5): 4111–4117; Feng et al 1997, Nat Biotechnol 15(9): 866–870; and UK Patent Application No. 9720465.5.

The term "derivable" is used in its normal sense as meaning the sequence need not necessarily be obtained from a retrovirus but instead could be derived therefrom. By way of example, the sequence may be prepared synthetically or by use of recombinant DNA techniques.

According to a second aspect of the present invention there is provided a viral particle obtainable from the retroviral delivery system according to the present invention.

According to a third aspect of the present invention there is provided a retroviral vector wherein the retroviral vector is the retroviral delivery system according to the first aspect of the present invention or is obtainable therefrom.

According to a fourth aspect of the present invention there is provided a cell transduced with a retroviral delivery system according to the present invention, or a viral particle according to the present invention, or a retroviral vector according to the present invention.

According to a fifth aspect of the present invention there is provided a retroviral delivery system according to the present invention, or a viral particle according to the present invention, or a retroviral vector according to the present invention, for use in medicine.

According to a sixth aspect of the present invention there is provided the use of a retroviral delivery system according to the present invention, or a viral particle according to the present invention, or a retroviral vector according to the present invention in the manufacture of a pharmaceutical composition to deliver a NOI to a target site in need of same.

According to a seventh aspect of the present invention there is provided a method comprising contacting a cell with a retroviral delivery system according to the present invention, or a viral particle according to the present invention, or a retroviral vector according to the present invention.

According to an eighth aspect of the present invention there is provided a vector for preparing a retroviral delivery system according to the present invention, or a viral particle according to the present invention, or a retroviral vector according to the present invention, wherein the vector comprises a nucleotide sequence coding for at least a part of the rabies G protein or a mutant, variant, derivative or fragment thereof.

According to a ninth aspect of the present invention there is provided a plasmid for preparing a retroviral delivery system according to the present invention, or a viral particle according to the present invention, or a retroviral vector according to the present invention, wherein the plasmid comprises a nucleotide sequence coding for at least a part of the rabies G protein or a mutant, variant, derivative or fragment thereof.

According to a tenth aspect of the present invention there is provided a plurality of plasmids, wherein at least one plasmid is a plasmid according to the present invention and wherein at least one other plasmid comprises one or more nucleotide sequences derivable from a retrovirus.

According to an eleventh aspect of the present invention there is provided the use of a rabies G protein to pseudotype a retrovirus or a retroviral vector or a retroviral particle in order to affect the infectious profile of the retrovirus or the retroviral vector or the retroviral particle.

According to a eleventh aspect of the present invention there is provided the use of a rabies G protein to pseudotype a retrovirus or a retroviral vector or a retroviral particle in order to affect the host range and/or cell tropism of the retrovirus or the retroviral vector or the retroviral particle.

According to a thirteenth aspect of the present invention there is provided a retrovirus or a retroviral vector or a retroviral particle pseudotyped with a rabies G protein.

According to a fourteenth aspect of the present invention there is provided a retroviral delivery system comprising a heterologous env region, wherein the heterologous env region comprises at least a part of a nucleotide sequence coding for a rabies G protein.

According to a fifteenth aspect of the present invention there is provided a retroviral delivery system comprising a heterologous env region, wherein the heterologous env region comprises a nucleotide sequence coding for a rabies G protein.

Preferably the first nucleotide sequence codes for all of a rabies G protein or a mutant, variant, derivative or fragment thereof.

Preferably at least one of the other nucleotide sequences is derivable from a lentivirus or an oncoretrovirus.

Preferably the other nucleotide sequences are derivable from a lentivirus or an oncoretrovirus.

Preferably the other nucleotide sequences are derivable from MLV, HIV or EIAV.

Preferably the retroviral delivery system comprises at least one NOI.

Preferably the NOI has a therapeutic effect or codes for a protein that has a therapeutic effect.

Preferably the target site is a cell.

Thus the present invention provides a retroviral vector having a heterologous envelope protein. This retroviral vector is useful in gene therapy.

An important aspect of the present invention is the pseudotyping of a retrovirus, and/or a retroviral vector derivable or based on same, with a nucleotide sequence coding for a rabies protein, especially the rabies G protein. Here, the term pseudotyping means incorporating in at least a part of, or substituting a part of, or replacing all of, an env gene of a viral genome, or of a viral vector, a protein from another virus.

Teachings on the rabies G protein, as well as mutants thereof, may be found in Rose et al., 1982 J. Virol. 43: 361–364, Hanham et al., 1993 J. Virol.,67, 530–542, Tuffereau et al.,1998 J. Virol., 72, 1085–1091, Kucera et al., 1985 J. Virol 55, 158–162, Dietzschold et al., 1983 PNAS 80, 70–74, Seif et al., 1985 J. Virol., 53, 926–934, Coulon et al.,1998 J. Virol., 72, 273–278, Tuffereau et al.,1998 J. Virol., 72, 1085–10910, Burger et al., 1991 J. Gen. Virol. 72. 359–367, Gaudin et al 1995 J Virol 69, 5528–5534, Bennansour et al 1991 J Virol 65, 41984203, Luo et al 1998 Microbiol Immunol 42, 187–193, Coll 1997 Arch Virol 142, 2089–2097, Luo et al 1997 Virus Res 51, 35–41, Luo et al 1998 Microbiol Immunol 42, 187–193, Coll 1995 Arch Virol 140, 827–851, Tuchiya et al 1992 Virus Res 25, 1–13, Morirnoto et al 1992 Virology 189, 203–216, Gaudin et al 1992 Virology 187, 627–632, Whitt et al 1991 Virology 185, 681–688, Dietzschold et al 1978 J Gen Virol 40, 131–139, Dietzschold et al 1978 Dev Biol Stand 40, 45–55, Dietzschold et at 1977 I Virol 23, 286–293, and Otvos et al 1994 Biochim Biophys Acta 1224, 68–76. A rabies G protein is also described in EP-A-0445625.

The use of rabies G protein according to the invention provides vectors which in vivo preferentially transduce targetted cells which rabies virus preferentially infects. This includes in particular neuronal target cells in vivo. For a neuron-targeted vector, rabies G from a pathogenic strain of rabies such as ERA may be particularly effective. On the other hand rabies G protein confers a wider target cell range in vitro including nearly all mammalian and avian cell types tested (Seganti el at., 1990 Arch Virol. 34,155–163; Fields et al., 1996 Fields Virology, Third Edition, vol.2, Lippincott-Raven Publishers, Philadelphia, N.Y.). It is likely that it will be found also to confer an ability to infect other cell types which will be of interest. Thus, the use of rabies G protein according to the invention also enables the provision of vectors which transduce a wide variety of cell types in vitro and also in vivo. The different tropism of rabies virus in vivo and in vitro is thought to be due to the ability of rabies G to bind to a series of receptors, some of which are only active in vitro.

Alternatively, the tropism of the pseudotyped vector particles according to the invention may be modified by the use of a mutant rabies G which is modified in the extracellular domain. Rabies G protein has the advantage of being mutatable to restrict target cell range. The uptake of rabies virus by target cells in vivo is thought to be mediated by the acetylcholine receptor (AchR) but there may be other receptors to which in binds in vivo (Hanham el al., 1993 J. Virol.,67, 530–542; Tuffereau et al.,1998 J. Virol., 72, 1085–1091). The effects of mutations in antigenic site III of the rabies G protein on virus tropism have been investigated, this region is not thought to be involved in the binding of the virus to the acetylcholine receptor (Kucera et al., 1985 J. Virol 55, 158–162; Dietzschold et al., 1983 Proc Natl Acad Sci 80, 70–74; Seif er al., 1985 J.Virol., 53, 926–934; Coulon et al.,1998 J. Virol., 72, 273–278; Tuffereau et al.,1998 J. Virol., 72, 1085–10910). For example a mutation of the arginine at amino acid 333 in the mature protein to glutamine can be used to restrict viral entry to olfactory and peripheral neurons in vivo while reducing propagation to the central nervous system. These viruses were able to penetrate motorneurons and sensory neurons as efficiently as the wt virus, yet transneuronal transfer did not occur (Coulon et al., 1989, J. Virol. 63, 3550–3554). Viruses in which amino acid 330 has been mutated are further attenuated, being unable to to infect either motorneurons or sensory neurons after intramuscular injection (Coulon et al.,1998 J. Virol., 72, 273–278).

Alternatively or additionally, rabies G proteins from laboratory passaged strains of rabies may be used. These can be screened for alterations in tropism. Such strains include the following:

| Genbank accession number | Rabies Strain |
| --- | --- |
| J02293 | ERA |
| U52947 | COSRV |
| U27214 | NY 516 |
| U27215 | NY771 |
| U27216 | FLA125 |
| U52946 | SHBRV |
| M32751 | HEP-Flury |

By way of example, the ERA strain is a pathogenic strain of rabies and the rabies G protein from this strain can be used for transduction of neuronal cells. The sequence of rabies G from the ERA strains is in the GenBank database (accession number J02293). This protein has a signal peptide of 19 amino acids and the mature protein begins at the lysine residue 20 amino acids from the translation initiation methionine. The HEP-Flury strain contains the mutation from arginine to glutamine at amino acid position 333 in the mature protein which correlates with reduced pathogenicity and which can be used to restrict the tropism of the viral envelope.

An example of a rabies G protein is shown as SEQ ID No. 2 and its coding sequence is presented as SEQ ID No. 1. The present invention covers variants, homologues or derivatives of those sequences.

The terms "variant", "homologue" or "fragment" in relation to the amino acid sequence for the preferred enzyme of the present invention include any substitution of, variation of, modification of, replacement of, deletion of or addition of one (or more) amino acid from or to the sequence providing the resultant protein has G protein activity and/or G protein characteristics or profile, preferably being at least as biologically active as the G protein shown as SEQ ID No. 2. In particular, the term "homologue" covers homology with respect to structure and/or function. With respect to sequence homology, preferably there is at least 75%, more preferably at least 85%, more preferably at least 90% homology to the sequence shown as SEQ ID No. 2. More preferably there is at least 95%, more preferably at least 98%, homology to the sequence shown as SEQ ID No. 2.

The terms "variant", "homologue" or "fragment" in relation to the nucleotide sequence coding for the preferred enzyme of the present invention include any substitution of, variation of, modification of, replacement of, deletion of or addition of one (or more) nucleic acid from or to the sequence providing the resultant nucleotide sequence codes for or is capable of coding for a protein having G protein activity and/or G protein characteristics or profile, preferably being at least as biologically active as the G protein encoded by the sequences shown as SEQ ID No. 1. In particular, the term "homologue" covers homology with respect to structure and/or function providing the resultant nucleotide sequence codes for or is capable of coding for a protein having G protein activity and/or G protein characteristics or profile. With respect to sequence homology, preferably there is at least 75%, more preferably at least 85%, more preferably at least 90% homology to the sequence shown as SEQ ID No. 1. More preferably there is at least 95%, more preferably at least 98%, homology to the sequence shown as SEQ ID No. 1.

In particular, the term "homology" as used herein may be equated with the term "identity". Relative sequence homology (i.e. sequence identity) can be determined by commercially available computer programs that can calculate % homology between two or more sequences. A typical example of such a computer program is CLUSTAL.

The terms "variant", "homologue" or "fragment" are synonymous with allelic variations of the sequences.

The term "variant" also encompasses sequences that are complementary to sequences that are capable of hybridising to the nucleotide sequence presented herein. Preferably, the term "variant" encompasses sequences that are complementary to sequences that are capable of hybridising under stringent conditions (e.g. 65° C. and 0.1 SSC {1× SSC=0.15 M NaCl, 0.015 $Na_3$ citrate pH 7.0}) to the nucleotide sequence presented herein.

The present invention also covers nucleotide sequences that can hybridise to the nucleotide sequence of the present invention (including complementary sequences of those presented herein). In a preferred aspect, the present invention covers nucleotide sequences that can hybridise to the nucleotide sequence of the present invention under stringent conditions (e.g. 65° C. and 0.1 SSC) to the nucleotide sequence presented herein (including complementary sequences of those presented herein).

A major advantage of using the rabies glycoprotein in comparison to the VSV glycoprotein is the detailed knowledge of its toxicity to man and other animals due to the extensive use of rabies vaccines. In particular phase 1 clinical trials have been reported on the use of rabies glycoprotein expressed from a canarypox recombinant virus as a human vaccine (Fries et al., 1996 Vaccine 14, 428–434), these studies concluded that the vaccine was safe for use in humans.

The retroviral vectors of the present invention are useful for the delivery of one or more NOIs to cells in vivo and in vitro, in particular the delivery of therapeutically active NOI(s). One or more selected NOI(s) may be incorporated in the vector genome for expression in the target cell. The NOI(s) may have one or more expression control sequences of their own, or their expression may be controlled by the vector LTRs. For appropriate expression of the NOI(s), a promoter may be included in or between the LTRs which is preferentially active under certain conditions or in certain cell types. The NOI may be a sense sequence or an antisense sequence. Furthermore, if there is a plurality of NOIs then those NOIs may be sense sequences or antisense sequences or combinations thereof.

The retroviral vector genome of the present invention may generally comprise LTRs at the 5' and 3' ends, one or more NOI(s) including therapeutically active genes and/or marker genes, or suitable insertion sites for inserting one or more NOI(s), and a packaging signal to enable the genome to be packaged into a vector particle in a producer cell. There may even be suitable primer binding sites and integration sites to allow reverse transcription of the vector RNA to DNA, and integration of the proviral DNA into the target cell genome. In a preferred embodiment, the retroviral vector particle has a reverse transcription system (compatible reverse transcription and primer binding sites) and an integration system (compatible integrase and integration sites).

Thus, in accordance with the present invention, it is possible to manipulate the viral genome or the retroviral vector nucleotide sequence, so that viral genes are replaced or supplemented with one or more NOIs. The NOI(s) may be any one or more of selection gene(s), marker gene(s) and therapeutic gene(s). Many different selectable markers have been used successfully in retroviral vectors. These are reviewed in "Retroviruses" (1997 Cold Spring Harbour Laboratory Press Eds: J M Coffin, S M Hughes, HE Varmus pp 444) and include, but are not limited to, the bacterial neomycin and hygromycin phosphotransferase genes which confer resistance to G418 and hygromycin respectively; a mutant mouse dihydrofolate reductase gene which confers resistance to methotrexate; the bacterial gpt gene which allows cells to grow in medium containing mycophenolic acid, xanthine and aminopterin; the bacterial hisD gene which allows cells to grow in medium without histidine but containing histidinol; the multidrug resistance gene (mdr)

which confers resistance to a variety of drugs; and the bacterial genes which confer resistance to puromycin or phleomycin. All of these markers are dominant selectable and allow chemical selection of most cells expressing these genes.

In accordance with the present invention, the NOI can be a therapeutic gene—in the sense that the gene itself may be capable of eliciting a therapeutic effect or it may code for a product that is capable of eliciting a therapeutic effect.

Non-limiting examples of therapeutic NOIs include genes encoding tumour supressor proteins, cytokines, anti-viral proteins, immunomodulatory molecules, antibodies, engineered immunoglobulin-like molecules, fusion proteins, hormones, membrane proteins, vasoactive proteins or peptides, growth factors, ribozymes, antisense RNA, enzymes, prorugs, such as pro-drug activating enzymes, cytotoxic agents, and enzyme inhibitors.

Examples of prodrugs include but are not limited to etoposide phosphate (used with alkaline phosphatase; 5-fluorocytosine (with cytosine deaminase); Doxorubin-N-p-hydroxyphenoxyacetarnide (with Penicillin-V-Amidase); Para-N-bis (2-chloroethyl)aminobenzoyl glutamate (with Carboxypeptidase G2); Cephalosporin nitrogen mustard carbamates (with B-lactamase); SR4233 (with p450 reductase); Ganciclovir (with HSV thyridine kinase); mustard pro-drugs with nitroreductase and cyclophosphamide or ifosfamide (with cytochrome p450).

Diseases which may be treated include, but are not limited to cancer, heart disease, stroke, neurodegenerative disease, arthritis, viral infection, bacterial infection, parasitic infection, diseases of the imrnune system, viral infection, tumours, blood clotting disorders, and genetic diseases—such as chronic granulomatosis, Lesch-Nyhan sysndrome, Parkinson's disease, empysema, phenylketonuria, sickle cell anaemia,$\alpha$-thalasemia, $\beta$-thalasemia, Gaucher disease.

Target cells for gene therapy using retroviral vectors include but are not limited to haematopoietic cells, (including monocytes, macrophages, lymphocytes, granulocytes, or progenitor cells of any of these); endothelial cells, tumour cells, stromal cells, astrocytes, or glial cells, muscle cells, epithelial cells, neurons, fibroblasts, hepatocyte. astrocyte, and lung cells.

Within the retroviral vector of the present invention, the one or more NOIs can be under the transcriptional control of the viral LTRs. Alternatively, a combination of enhancer-promotcr elements can be present in order to achieve higher levels of expression. The promoter-enhancer elements are preferably strongly active or capable of being strongly induced in the target cells. An example of a strongly active promoter-enhancer combination is a human cytomegalovirus (HCMV) major intermediate early (MIE) promoter/enhancer combination. The promoter-enhancer combination may be tissue or temporally restricted in their activity. Examples of a suitable tissue restricted promoter-enhancer combinations are those which are highly active in tumour cells such as a promoter-enhancer combination from a MUCI gene or a CEA gene.

Hypoxia or ischaemia regulatable expression may also be particularly useful under certain circumstances. Hypoxia is a powerful regulator of gene expression in a wide range of different cell types and acts by the induction of the activity of hypoxia-inducible transcription factors such as hypoxia inducible factor-1 (HIF-1) (Wang and Semenza 1993 PNAS. (USA) 90: 430) which bind to cognate DNA recognition sites, the hypoxia responsive elements (HREs) on various gene promoters. A multimeric form of HRE from the mouse phosphoglycerate kinase-1 (PGK-1) gene has been used to control expression of both marker and therapeutic genes by human fibrosarcoma cells in response to hypoxia in vitro and within solid tumours in vivo (Firth et al 1994, PNAS 91(14): 6496–6500; Dachs et al 1997 Nature Med. 5: 515).

Alternatively, the fact that glucose deprivation is also present in ischaemic areas of tumours can be used to activate heterologous gene expression especially in tumours. A truncated 632 base pair sequence of the grp 78 gene promoter, known to be activated specifically by glucose deprivation, has been shown to be capable of driving high level expression of a reporter gene in murine rumours in vivo (Gazit et al 1995 Cancer Res. 55: 1660.).

The relroviral vector genomes of the present invention for subsequent use in gene therapy preferably contain the minimum retroviral material necessary to function efficiently as vectors. The purpose of this is to allow space for the incorporation of the NOI(s), and for safety reasons. Retroviral vector genomes are preferably replication defective due to the absence of functional genes encoding one or more of the structural (or packaging) components encoded by the gag-pol and env genes. The absent components required for particle production are provided in trans in the producer cell. The absence of virus structural components in the genome also means that undesirable immune responses generated against virus proteins expressed in the target cell are reduced or avoided. Furthermore, possible reconstruction of infectious viral particles is preferably avoided where in vivo use is contemplated. Therefore, the viral structural components are preferably excluded from the genome as far as possible, in order to reduce the chance of any successful recombination.

The retroviral vector particles of the present invention are typically generated in a suitable producer cell. Producer cells are generally mammalian cells but can be for example insect cells. A producer cell may be a packaging cell containing the virus structural genes, normally integrated into its genome. The packaging cell is then transfected with a nucleic acid encoding the vector genome, for the production of infective, replication defective vector particles. Alternatively the producer cell may be co-transfected with nucleic acid sequences encoding the vector genome and the structural components, and/or with the nucleic acid sequences present on one or more expression vectors such as plasmids, adenovirus vectors, herpes viral vectors or any method known to deliver functional DNA into target cells.

In accordance with a highly preferred embodiment of the present invention, we surprisingly discovered that the envelope protein from rabies virus, the rabies G protein, can efficiently pseudotype a wide variety of retroviral vectors. These include not only vectors constructed from murine oncoretroviruses such as MLV, but also vectors constructed from primate lentiviruses such as HIV and from non-primate lentiviruses such as equine infectious anaemia virus (EIAV).

In one embodiment, the vector of the present invention is constructed from or is derivable from a lentivirus. This has the advantage that the vector may be capable of transducing non-dividing cells and dividing cells.

Thus, the preferred retroviral vectors for pseudotyping according to the invention are lentivirus vectors such as HIV or EIAV vectors. These have the advantages noted above. In particular a rabies G pseudotyped lentivirus vector having rabies virus target cell range will be capable of transducing non-dividing cells of the central nervous system such as neurons.

The findings of the present invention are highly surprising. In this respect, although rabies and VSV are Rhabdoviridae, which is a very large family containing five diverse sub-groups, they (i.e. VSV and rabies) are in different sub-groups. Moreover, the rabies G protein has little homology with VSV-G (Rose et al., 1982 J. Virol. 43: 361–364). The rabies G protein also has a much longer cytoplasmic domain than VSV-G, of normally about 44 amino acids (in length) compared with the 28 to 31 amino acid VSV-G cytoplasmic domain. The finding that the rabies G protein is able to pseudotype MLV is therefore unexpected, given that truncation of the 144 amino acid HIV-1 cytoplasmic tail was required for efficient pseudotyping of MLV particles (Mamnmano et al., 1997 J. Virol. 71:3341–3345). It is also surprising that the rabies G protein can additionally pseudotype other retroviruses such as viruses in the lentivirus group.

The invention therefore provides in one aspect a retroviral vector particle pseudotyped with a rabies virus G protein.

In another aspect, the invention provides a retroviral vector production system comprising a nucleic acid sequence which encodes a rabies virus G protein, a nucleic acid sequence which encodes a retrovirus vector genome and optionally one or more further nucleic acid sequences which encode packaging components required for the generation of infective retroviral vector particles containing the genome.

In a further aspect, the invention provides the use of a rabies virus G protein to alter the target cell range of a retroviral vector.

In another aspect, the invention provides a method of producing retroviral vector particles having an envelope comprising rabies virus ( protein, which method comprises providing a retroviral vector production system as described herein, in a producer cell, subjecting the producer cell to conditions suitable for the expression of vector particle components and the production of vector particles, and harvesting the vector particles from the supernatant.

In yet another aspect, the invention provides a method of transducing a target cell with a NOI, which method comprises contacting the cell with a retroviral vector particle as described herein, carrying the NOI, under conditions to allow attachment to and entry of the vector into the cell such that the NOI enters :the target cell genome.

In addition to the rabies G protein present in the envelope of a vector according to the invention, one or more other envelope proteins may also be present. This may include for example a native envelope protein of the retrovirus. The use of a native envelope protein in addition to a pseudotyping protein can be beneficial to the stability and/or function of the envelope. It may even broaden the infectious profile of the vector.

The present invention also provides a pharmaceutical composition for treating an individual by gene therapy, wherein the composition comprises a therapeutically effective amount of a retroviral vector according to the present invention. The pharmaceutical composition may be for human or animal usage. Typically, a physician will determine the actual dosage which will be most suitable for an individual subject and it will vary with the age, weight and response of the particular patient.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant (s), suspending agent(s), coating agent(s), solubilising agent (s), and other carrier agents that may aid or increase the viral entry into the target site (such as for example a lipid delivery system).

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Thus, in summation, the present invention relates to a retroviral vector having a heterologous envelope protein, in particular a rabies virus G protein. The present invention also relates to a retroviral vector production system for the production of retroviral vectors having an envelope comprising a rabies virus G protein, as well as to methods of producing the vector and the systems, and to methods involving the use of the vector and the systems.

The present invention will now be described by way of example only, and with reference to the following Figures—in which:

BRIEF DESCRIPTION OF THE DRAWINGS

FIG. 1 presents a plasmid map;

FIG. 2 presents a photograph of a gel;

FIG. 3 presents a set of schematic diagrams;

FIG. 4 presents a graph;

FIG. 5 presents two graphs; and

FIG. 6 presents a schematic diagram.

EXAMPLE 1

Production of Vectors Expressing Rabies G Protein and Details of Other Vectors Used An expression vector for rabies G was constructed by cloning 1.7 kbp BglII rabies G fragment (strain ERA) from pSG5rabgp (Burger et al., 1991 J.Gen. Virol. 72. 359–367) into pSA91 (FIG. 1), a derivative of pGW1HG (Soneoka el al 1995 Nuct. Acids Res. 23: 628–633) from which the gpt gene has been removed by digestion with BamHI and re-ligation. This construct, pSA91RbG, allows expression of rabies G from the human cytomegalovirus (HCMV) immediate early gene promoter-enhancer. The plasmid was transfected, in conjunction with pONY3 (see details for construction later) and pONY2.1nlsLacZ (see details for construction later), into 293T cells by the method described by Soneoka et al 1995 (ibid) and expression of rabies G in transfected cells was confirmed by Western blotting. A VSV-G expression plasmid, in which VSV-G was expressed under the control of HCMV, in place of rabies G in pSA91 was used as a negative control. Transfected cells were washed with PBS, lysed in RIPA buffer containing 1 mM freshly prepared PMSF and total protein concentration determined using BCA protein quantification reagent kit (BCA Inc., USA) as per the manufacturer's specifications. 50 $\mu$g of cell lysate was run on 10% SDS/PAGE. The gels were electroblotted onto the immobilon membrane (Millipore Inc). Western blot analysis was carried out with 17D2, a mouse monoclonal antibody against rabies G at a dilution of 1:3000 and rabbit peroxidase conjugated anti-mouse IgG at a dilution of 1:1000 (Vector Laboratories, Peterborough, UK). Detection by chemiluminescence was performed using ECL kit (Amersham International, UK). A 68 kD band corresponding to the reported size for rabies G is apparent in cells transfected with pSA91RbG (FIG. 2).-

In all of the following examples the three plasmid transfection method as described previously (Soneoka et al., 1995, ibid) was used to generate pseudotyped vectors. The plasmids used in these experiments were as follows. pHIT111 and pHIT60 express an MLV vector containing the E.coli lacZ marker gene and MLV gag-pol respectively (Soneoka et al., 1995). pH3Z and pGP-RRE3 are the corresponding HIV vector components (Kim et al., 1998 J. Virol. 72:811–816). pONY2.1nlsLacZ and pONY3 are the corresponding EIAV vector components (GB patent application 9727135.7). The important features of these vectors are shown in FIG. 3, which includes features of the EIAV vectors.

The description of abbreviations and labels used in FIG. 3 are as follows:

| | |
|---|---|
| CMV | human cytomegalovirus immediate-early enhancer/promoter region |
| SV40 | simian virus 40 enhancer and early promoter region |
| LTR | long terminal repeat |
| R | repeat region of the LTR |
| U3 | 3 prime unique sequence of the LTR |
| ΔU3 | an incomplete U3 sequence. |
| U5 | 5 prime unique sequence of the LTR |
| Ψ | genome packaging signal |
| tat | regulatory protein |
| rev | regulatory protein |
| RRE | rev response element |
| env | gene encoding for the envelope protein |
| Δenv | env gene containing a deletion such that a truncated protein product is produced |
| gag | region encoding for the capsid proteins |
| Δgag | gag region containing a deletion such that an incomplete series of capsid proteins are produced |
| pol | region encoding for the enzymatic proteins |
| vif | viral infectivity factor |
| pA | polyadenlyation signal |
| lacZ | gene encoding for β-galactosidase |
| neo | gene encoding for neomycin phosphotransferase |

Construction of the EIAV vectors was as follows.

An infectious proviral clone, pSPEIAV19, as described by Payne et al. (1994, J.Gen. Virol. 75:425–9) was used as a starting point. A plasmid, pSPEIAVΔH, was constructed by the deletion of a HindIII fragment, 5835–6571, from the region of the plasmid encoding for the envelope protein. A vector genome plasmid was constructed by inserting the ELAV LTR, amplified by PCR from pSPEIAV19, into pBluescript II KS+(Stratagene). The MluI/MluI (216/814) fragment of pSPEIAVΔH was then inserted into the LTR/Bluescript plasmid to generate pONY2. In addition, a BglII/NcoI fragment within pol (1901/4949) was deleted and a nuclear localising β-galactosidase gene driven by the HCMV IE enhancer/promoter was inserted in its place. This was designated pONY2.1nlsLacZ.

An EIAV plasmid (pONY3) encoding the gagpol genes was then made by inserting the MluI/MluI fragment from pONY2ΔH into the mammalian expression plasmid pCI-neo (Promega) such that the gag-pol protein is expressed from the HCMV IE enhancer/promoter.

| Gag-pol expression vector | lacZ-containing vector | Viral vector type |
|---|---|---|
| pHIT60 | pHIT111 | MLV |
| pGP-RRE1 | pH3Z | HIV |
| pONY3 | pONY2.1nlsLacZ | EIAV |

EXAMPLE 2

Pseudotyping Retroviral Vectors with Rabies G Protein

The three plasmid transfection method as described previously (Soneoka el al 1995) was used to generate pseudotyped vectors. In initial experiments, 10 μg of pSA91RbG was co-transfected with 10 μg each of a gag-pol expressing plasmid and a retroviral vector capable of expression of the E. coli lacZ gene per well of a 6-well tissue culture dish. Pseudotyping with VSV-G was used as a positive control for these experiments by using 10 μg of pRV67, a VSV-G expression plasmid in which VSV-G was expressed under the control of human cytomegalovirus promoter/enhancer, in place of rabies G in pSA91.

Transfections were carried out in the human kidney cell line 293T (as described in Soneoka et al., 1995) to produce the vector virions. Culture supernatants were harvested 36h post transfection and filtered through 0.45 mm pore-size filters (Millipore).

In contrast with the neuronal specificity of rabies in vivo, it is known that laboratory strains of rabies virus can interact with a wider variety of cell lines in vitro (Reagan and Wunner 1985 Arch. Virol. 84:277–282). Two cell lines, BHK21 cells, a baby hamster kidney cell line and D17 cells, a dog melanoma cell line were therefore evaluated for use as target cells for retroviral vectors pseudotyped with rabies G.

Cells were seeded into 6-well tissue culture plates the day before infection at $3 \times 10^5$ cells per well. Viral supernatant prepared by transfecting 293T cells with appropriate plasmids to pseudotype EIAV, HIV-1 and MLV vectors as described above was added to these cells. Polybrene (8 μg/ml) was added to each well at the time of transduction into 1 ml of the culture supernatant used for infection. 12 hours post infection, the culture supernatant was replaced by fresh medium. To measure the viral titre, cells are washed, fixed and stained 48 hours post infection.

We could observe β-galactosidase positive colonies of D17 cells in case of transfections with pSA91RbG and pRV67 with all of the three retroviral vector constructs. There were no β-galactosidase positive colonies in transfections without either pSA91RbG or pRV67 indicating that an envelope is required for transduction to occur. In case of infections with BHK21 cells we could observe β-galactosidase positive colonies only in case of MLV pseudotypes but not with the EIAV and HIV-1 pseudotypes. This inability could be due to post-binding blocks for EIAV and HIV-1 in this cell type. These results establish that rabies G can pseudotype EIAV, HIV and MLV vectors.

The efficiency of pseudotyping was studied by comparing the viral titres for these pseudotyped vectors. Viral titres were estimated from the number of β-galactosidase positive colonies (Table 1).

TABLE 1

Relative efficiencies of pseudotyping retroviral vectors with rabies G protein

| Retro viral vector | Viral components | | | | Number of transducing particles per ml as assessed on the following cells | |
|---|---|---|---|---|---|---|
| | Corresponding plasmid construct | Gag-pol expression plasmid | Envelope expression plasmid | Resulting pseudotyped vectors | D17 | BHK-21 |
| 1 EIAV | pONY2.lnlsLacZ | pONY3 | pRV67 | EIAV-VSVG | $8.4 \times 10^4$ | $<10^1$ |
| 2 EIAV | pONY2.lnlsLacZ | pONY3 | pSA91RbG | EIAV-RbG | $3.2 \times 10^4$ | $<10^1$ |
| 3 HIV | pH4Z | pGP-RRE1 | pRV67 | HIV-VSVG | $3.0 \times 10^4$ | $<10^1$ |
| 4 HIV | pH4Z | pGP-RRE1 | pSA91RbG | HIV-RbG | $6.4 \times 10^3$ | $<10^1$ |
| 5 MLV | pHIT111 | pHIT60 | pRV67 | MLV-VSVG | $6.3 \times 10^6$ | $4.8 \times 10^6$ |
| 6 MLV | pHIT111 | pHIT60 | pSA91RbG | MLV-RbG | $1.6 \times 10^6$ | $7.8 \times 10^6$ |
| 7 Mock | — | — | — | — | $<10^1$ | $<10^1$ |

Viral titre for MLV pseudotyped with rabies G is comparable to that observed for VSV-G pseudotypes in both the cell lines tested ($4.8 \times 10^6$ and $7.8 \times 10^6$, in BHK21 for VSV-G and rabies G respectively; $6.3 \times 10^6$ and $1.6 \times 10^6$ in D17 cells for VSV-G and rabies G respectively).

Similar results were obtained in the case of EIAV and HIV-1 pseudotyped with VSV-G and rabies G in D17 cells. In the case of EIAV viral titres for the vector pseudotyped with VSV-G and rabies G were $8.4 \times 10^4$ and $3.2 \times 10^4$ respectively. In HIV-1, viral titres were $3.0 \times 10^4$ and $6.4 \times 10^3$ in the case of pseudotypes with VSV-G and rabies G respectively. These results indicate that rabies G is essentially as efficient as VSV-G in pseudotyping with all of the three retroviral vectors.

Our results demonstrate that rabies & protein can pseudotype retroviral vectors EIAV, HIV-1 and MLV with very high titres comparable to those obtained with VSV-G.

EXAMPLE 3

Production and Characterisation of a Rabies G Protein with an Altered Amino Acid 333

The coding sequence of the rabies glycoprotein gene in pSA91RbG was engineered, using overlap PCR, so that the resultant protein possesses a glutamate at position 333 rather than an arginine. This change has been reported to cause attenuation and altered cell tropism in rabies viruses. The primers used for mutagenesis were as follows:

forward primer (SEQ ID No:3)

5' GATGCTCACTACAAGTCAGTCCAGACTTGG AATGAGA³TCCTCCC reverse primer (SEQ ID No:4)

5' GGGAGGATCTCATTCCAAGTCTGGACTGAC TTGTAGT³GAGCATC

The engineered fragment was reintroduced into pSA91Rg as a Sphl BglII fragment, the resultant plasmid being pSA91RM. The engineered rabies G protein produced from this vector was tested for its ability to pseudotype MLV particles. The plasmid was transfected, in conjunction with pHIT60 and pHIT111, into 293T cells as described by Soneoka et at 1995; pSA91Rg was used as a positive control. The supernatants from these transfections were harvested as previously described, and the ability of the two envelopes to pseudotype MLV particles was assessed by their ability to transduce either BHK-21 or a murine neuroblastoma cell line, C-1300 clone NA (Table 2).

TABLE 2

Characterisation of the ability of a rabies G protein with an altered amino acid 333 to pseudotype MLV particles

| Retro viral vector | Viral components | | | | Number of transducing particles per ml as assessed on the following cells | |
|---|---|---|---|---|---|---|
| | Corresponding plasmid construct | Gag-pol expression plasmid | Envelope expression plasmid | Resulting pseudotyped vectors | BHK21 | C-1300 |
| 1 MLV | pHIT111 | pHIT60 | pSA91RbG | MLV-RbG | $4.2 \times 10^6$ | $6.1 \times 10^6$ |
| 2 MLV | pHIT111 | pHIT60 | pSA91RM | MLV-RMG | $3.1 \times 10^5$ | $7.2 \times 10^6$ |
| 3 Mock | — | — | — | — | $<1$ | $<1$ |

Although the titre obtained on BHK-21 cells, a cell line that is commonly used to produce rabies vaccines, was lower with engineered rabies G protein than with the wt, comparable titres were obtained for the two envelopes on C-1300 cells. These results indicate that the engineered protein is efficiently capable of pseudotyping MLV particles.

EXAMPLE 4

Optimisation of Titre of Rabies G Pseudotyped Retroviral Vectors

The amount of pSA91RbG DNA added to the 3-plasmid transfection system was titrated against the other two components in order to determine the optimum viral titre.

In this experiment, COS-1 cells were transfected using $CaPO_4$ precipitation with the plasmids, pSA91RbG, pHIT111, and pHIT60. The latter two plasmids were used in equal amounts (8 μg per transfection per 35mm tissue culture dish) whilst the amount of pSA91RbG was serially reduced. The supernatants from the transfections were harvested at 36 hours post transfection and the number of transducing particles present was determined on HT1080 cells. The results are shown in FIG. 4. An eight-fold reduction in the amount of pSA91RbG DNA in comparison to the other plasmids was found to produce the highest titres. Titres overall were lower than obtained from 293T cells in Example 1.

Titration of pSA91RbG against the two components required to produce EIAV-based vectors was also carried out. In this case, 293T cells were transfected using $CaPO_4$ precipitation with 8 μg plasmid encoding the gag/pol (pONY3) and 8 μg plasmid expressing the EIAV vector encoding for β-galactosidase (pONY2.11nlacZ). Varying amounts of pSA91RbG or pRV67 were added as above to provide vectors pseudotyped with rabies G or VSV-G respectively. The supernatants from the transfections were harvested at 36 hours post transfection and the numbers of transducing particles present was determined on D17 cells. The results are shown in FIG. 5. A two- to four-fold reduction in the amount of pSA91RbG DNA in comparison to the other plasmids was found to produce the highest titres. No significant reduction in titre was observed when pRV67 was used in equal amounts to the other two plasmids.

These results show that it is possible to obtain improved titres of rabies G pseudotyped retroviral vectors by adjusting the relative amounts of rabies G and other vector components expressed in the producer cell.

EXAMPLE 5

Concentration of Rabies G Pseudotyped Retroviral Vectors

We have further investigated whether we can increase the viral titre by concentrating the viral supernatant using ultracentrifugation (Burns er al., 1993 PNAS 90:8033–8037) obtained a viral titre of $10^9$ transducing particles per ml with VSV-G pseudotyped MLV based vector upon ultracentrifugation.

The three plasmid transfection method as described previously (Soneoka et al., 1995) was used to generate particles pseudotyped with either rabies G or VSV-G. Transducing particles were harvested 36 hours after transfection, concentrated by ultracentrifugation and titred on D17 cells. 48 hours later these cells were stained for β-galactosidase. Titres were averaged from three independent experiments and calculated as β-galactosidase producing units per ml. There was no more than 10% variation between experiments. It proved possible to decrease the volume of the harvests by 130 fold with out an appreciable loss of transducing particles for both EIAV and MLV particles pseudotyped with either of the two envelopes (Table 3).

TABLE 3

The effect of concentration on rabies G pseudotyped retroviral vectors.

| Viral components | | | | | Titre | Titre | Fold | Fold | |
|---|---|---|---|---|---|---|---|---|---|
| Retro-viral vector | Corresponding plasmid construct | Gag-pol expression plasmid | Envelope expression plasmid | Resulting pseudotyped vectors | before concen-tration | after concen-tration | decrease in volume | increase in titre | Recovery (%) |
| EIAV | pONY2.1nls LacZ | pONY3 | pRV67 | EIAV-VSVG | $2.0 \times 10^5$ | $2.5 \times 10^7$ | 130 | 125 | 96 |
| EIAV | pONY2.1nls LacZ | pONY3 | pSA91RbG | EIAV-RbG | $1.0 \times 10^5$ | $1.2 \times 10^7$ | 130 | 120 | 96 |
| EIAV | pONY2.1nls LacZ | pONY3 | Mock | | <1 | <1 | 130 | N.A. | N.A. |
| MLV | pHIT111 | pHIT60 | pRV67 | MLV-VSVG | $4.0 \times 10^5$ | $4.8 \times 10^7$ | 130 | 119 | 92 |
| MLV | pHIT111 | pHIT60 | pSA91RbG | MLV-RbG | $3.5 \times 10^5$ | $4.5 \times 10^7$ | 130 | 128 | 98 |
| MLV | pHIT111 | pHIT60 | Mock | | <1 | <1 | 130 | N.A. | N.A. |

These results indicated that vectors pseudotyped with rabies G can be concentrated upon ultracentrifugation with an increase in the vector titre comparable to that observed for VSV-G.

These properties together with the in vivo specificity of the rabies G for neuronal cells make pseudotyping with the rabies G an attractive proposal for easy targeting of retroviral vectors carrying any therapeutic gene to the nervous system.

EXAMPLE 6

Selectivity of the Ability of Rabies G Pseudotypes to Transduce Cultured Human Target Cells.

The cell specificity of vectors pseudotyped with rabies G was determined using human cell lines of neuronal and non-neuronal origin. Pseudotyping with VSV-G was used as a positive control. Viral supernatant prepared from three plasmid transfection was used to infect IMR-32, a human neuroblastoma cell line and CEM-A, a human T cell line. Viral titres are estimated from -galactosidase positive colonies (Table 4).

TABLE 4

Selectivity of the ability of rabies pseudotypes to transduce cultured human target cells

| Retro viral vector | Viral components | | | | Number of transducing particles per ml as assessed on the following cells | |
|---|---|---|---|---|---|---|
| | Corresponding plasmid construct | Gag-pol expression plasmid | Envelope expression plasmid | Resulting pseudotyped vectors | IMR32 | CEM-A |
| 1 MLV | pHIT111 | pHIT60 | pRV67 | MLV-VSVG | $4.9 \times 10^3$ | $7.3 \times 10^2$ |
| 2 MLV | pHIT111 | pHIT60 | pSA91RbG | MLV-RbG | $3.1 \times 19^3$ | $1.7 \times 10^1$ |
| 3 Mock | — | — | — | — | 0 | 0 |

MLV vector pseudotyped with rabies G and VSV-G could infect the IMR-32 cells. However MLV vector pseudotyped with rabies G produced titres 100 times higher ($3.1 \times 10^5$) than the same with VSV-G ($4.9 \times 10^3$). In CEM-A cells, MLV vector pseudotyped with rabies G gave a low titre of $1.7 \times 10^1$. This low efficiency was not due to the inability of MLV to transduce these cells. This is evident by the comparatively higher titre for the same vector when pseudotyped with VSV-G ($7.3 \times 10^2$)

Our results demonstrate that unlike VSV-G, rabies G pseudotypes show selectivity in their ability to transduce human target cells, with higher transduction efficiencies in neuronal cells than in the T-cell line.

EXAMPLE 7

The Ability of Rabies G Pseudotypes to Transduce Brain Cells in Vitro (Primary Cultures) and in Vivo (Ratimouse Model Systems)

There is evidence to suggest that at least two different receptors are used by rabies virus in vivo (Hanham et al., 1993 J. Virol. 67:530–542; Tuffereau et al., J. Virol. 72:1085–1091), one of these receptors may be the nicotinic acetylcholine receptor. Detailed studies on the types of neuronal cells infected and the spread of the virus throughout the nervous system have been carried out with wt rabies (CVS strain) and with a double mutant of this strain (altered at amino acids 330 and 333) in mouse model systems (Coulon et al., 1989 J. Virol. 63:3550–3554; Lafay et al., 1991 Virology 183;320–330). These studies have shown that the spread and range of the mutated virus is significantly restricted in comparison to the wt.

To determine the tropism of EIAV vectors pseudotyped with rabies G protein, the following analyses are undertaken. Adult female AO rats are anaesthetized and stereotaxically injected with $2 \times 1 \mu l$ of viral stock into striatum or other brain regions. 7 or 30 days post-injection the rats are anaesthetized and perfused intracardially with 4% paraformaldehyde. The brains are removed, postfixed for 24 hours, saturated in 30% sucrose and sectioned on a freezing cryostat (50 $\mu$m). Sections are strained with X-gal solution for 3 hours to overnight, mounted on to glass slides and analyzed with the light microscope. Identification of specific cell types transduced is made by immunofluorescence triple labeling using antibodies specific to neurons (NeuN or others), astrocytes (GFAP) or oligodendrocytes (GalC) and β-galactosidase in combination with species-specific secondary antibodies. Imaging of transduced brain regions are analyzed using confocal microscopy.

For in vitro transduction experiments primary neurons are put in culture from rat embryos and are grown until fully differentiated. Viral vectors are added for 5 hours using polybrene at 4 $\mu$g/ml. Media are changed and expression analysis is carried out 2 days later either using X-gal staining or antibodies.

EXAMPLE 8

Concentration of Rabies G Pseudotyped HIV-1 Vectors and Comparison between the Use of the VSV-G and Rabies Envelopes to Produce Such Vectors Example 5 demonstrates that EIAV vectors pseudotyped with rabies -G can be efficiently concentrated by ultracentrifugation in the same manner as has been reported with VSV-G pseudotyped vectors. We have extended these observations to show that rabies G can be used to pseudotype HIV-1 vectors, that these particles may be efficiently concentrated by ultracentrifugation and that titres obtained on D17 cells may be obtained that are equivalent to those obtained with VSV-G pseudotyped vectors.

The three plasmid transfection method as described previously (Soneoka et al., 1995) was used to generate particles pseudotyped with either rabies G or VSV-G. The HIV-1 plasmids, pH4Z and pGP-RRE3, used in this experiment have been discribed in Kim et al. (1998 Journal of Virology 72: 811–816). The ratio of the components used in this experiment was 1:1:1, gag/pol:genome:envelope for rabies G and 1:1:0.5, gag/pol:genome:envelope for VSV-G; this is at variance with the ratios used for COS 1 cells, since we have found that 293T cells are more resistant to the expression of the rabies G protein than COS cells. Transducing particles were harvested 48 hours after transfection, concentrated by ultracentrifugation and titred on D17 cells. 48 hours later these cells were stained for b-galactosidase. It proved possible to increase the titre of the harvests by approximately 100 with HIV-1 particles pseudotyped with either of the two envelopes (Table 5). The tires obtained for vectors pseudotyped with either of the envelopes were not significantly different. These results indicated that vectors pseudotyped with rabies G can be concentrated upon ultracentrifuigation with an increase in the vector titre comparable to that observed for VSV-G and that the two envelopes are similarly effective on D17 cells.

TABLE 5

| Preparation. | LacZ colony forming units per 0.5 mL | | Mean titre per ml. |
|---|---|---|---|
| Rabies pseudotyped HIV-1 before concentration. | $3.4 \times 10^5$ | $4.1 \times 10^3$ | $7.5 \times 10^6$ |

TABLE 5-continued

| Preparation. | LacZ colony forming units per 0.5 mL | | | Mean titre per ml. |
|---|---|---|---|---|
| Rabies pseudotyped HIV-1 after concentration. | $3.5 \times 10^6$ | $3.3 \times 10^8$ | $3.6 \times 10^8$ | $6.9 \times 10^8$ |
| VSV-G pseudotyped HIV-1 before concentration. | $3.7 \times 10^6$ | $4.0 \times 10^6$ | | $7.7 \times 10^6$ |
| VSV-G pseudotyped HIV-1 after concentration. | $4.8 \times 10^8$ | $4.6 \times 10^8$ | $3.9 \times 10^8$ | $8.9 \times 10^8$ |

Discussion and Summary

As indicated earlier, retroviruses and vectors derived from them require a specific envelope protein in order to efficiently transduce a target cell. The envelope protein is expressed in the cell producing the virus or vector and becomes incorporated into the virus or vector particles. Retrovirus particles are composed of a proteinaceous core dervived from the gag gene that encases the viral RNA. The core is then encased in a portion of cell membrane that contains an envelope protein derived from the viral env gene. The envelope protein is produced as a precursor, which is processed into two or three units. These are the surface protein (SU) which is completely external to the envelope, the transmembrane protein (TM) which interacts with the SU and contains a membrane spanning region and a cytoplasmic tail (Coffin 1992 In The Retroviridae, Pleum Press, ed Levy). In some retroviruses a small peptide is removed from the TM. In order to act as an effective envelope protein, capable of binding to a target cell surface and mediating viral entry, the envelope protein has to interact in a precise manner with the appropriate receptor or receptors on the target cell in such a way as to result in internalisation of the viral particle in an appropriate manner to deliver the genome to the correct compartment of the cell to allow a productive infection to occur.

There have been many attempts to use the envelope derived from one virus to package a different virus, this is known as pseudotyping. The efficiency of pseudoryping is highly variable and appears to be strongly influenced by interactions between the cytoplasmic tail of the envelope and the core proteins of the viral particle. The process by which envelope proteins are recruited into budding virions is poorly understood, although it is known that the process is selective since most cellular proteins are excluded from retroviral particles (Hunter 1994 Semin. Virol. 5:71–83) and it has been recorded in some retroviruses that budding may occur in the absence of envelope proteins (Einfeld 1996 Curr. Top. Microbiol. Immunol. 214:133–176; Krausslich and Welker 1996 Curr. Top. Microbiol. Imrnunol. 214:25–63). There is evidence for a precise molecular interaction between a cytoplasmic domain of the envelope protein and the viral core in some retroviruses. Januszeski et al (1997 J. Virol. 71: 3613–3619) have shown that minor deletions or substitutions in the cytoplasmic tail of the murine leukemia virus (MLV) envelope protein strongly inhibit incorporation of the envelope protein into viral particles. In the case of HIV-1, Cosson (1996 EMBO J. 15:5783–5788) has shown a direct interaction between the matrix protein of HIV-1 and the cytoplasmic domain of its envelope protein. This interaction between the matrix and envelope protein plays a key role in the incorporation of the envelope protein into budding HIV-1 virions. This is shown by the fact that visna virus can only be efficiently pseudotyped with HIV-1 Env if the amino terminus of the matrix domain of the visna virus gag polyprotein is replaced by the equivalent HIV-1 matrix domain (Dorfinan et al., 1994 J. Virol. 68:1689–1696). However the situation is complex, since truncation of the HIV-1 Env is required for efficient psuedotyping of Molony murine leukemia virus (Marnnano et al., 1997 J. Virol. 71:3341–3345), whilst truncation of the human foamy virus envelope protein reduced its ability to pseudotype murine leukemia virus (Lindemann et al., 1997 J. Virol. 71:481–54820). There is also an environmental component to the interaction between the core of a retrovirus and the cytoplasmic tail of its envelope protein. Prolonged passage of EIAV in some cell lines results in a truncation of the glycoprotein, suggesting that host cell factors can select for a virus on the basis of the C-terminal domain of the envelope protein (Rice et al., 1990 J. Virol. 1990 64: 3770–3778).

These studies and those of many other workers indicate that it is not possible to predict that even closely related retroviruses may be able to pseudotype each other. Further more, if a given envelope fails to pseudotype a particular virus, it is not possible to predict the molecular changes that would confer the ability to pseudotype. Pseudotyping has met with some success, but is clearly constrained by the need for compatibility between the virus components and the heterologous envelope protein.

In the construction of retroviral vectors it is desirable to engineer vectors with different target cell specificities to the native virus, to enable the delivery of genetic material to an expanded or altered range of cell types. One manner in which to achieve this is by engineering the virus envelope protein to alter its specificity. Another approach is to introduce a heterologous envelope protein into the vector to replace or add to the native envelope protein of the virus.

The MLV envelope protein is capable of pseudotyping a variety of different retroviruses. MLV envelope protein from an amphotropic virus allows transduction of a broad range of cell types including human cells. However, it may not always be desirable to have a retroviral vector which infects a large number of cell types.

The envelope glycoprotein (G) of Vesicular stomatis virus (VSV), a rhabdovirus, is another envelope protein which has been shown to be capable of pseudotyping certain retroviruses. The retrovirus MLV was successfully pseudotyped (Burns et al 1993 Proc. Natl. Acad. Sci. USA 90: 8033–7) and resulted in a vector having an altered host range compared to MLV in its native form. VSV-G pseudotyped vectors have been shown to infect not only mammalian cells, but also cell lines derived from fish, reptiles and insects (Burns et al 1993). VSV-G protein can be used to pseudotype certain retroviruses because its cytoplasmic tail is capable of interacting with the retroviral cores. VSV-G and MLV envelope proteins, both have short cytoplasmic tails, 28 to 31 and 32 amino acids respectively, and are thus of very similar length.

The provision of a non-retroviral pseudotyping envelope such as VSV-G protein gives the advantage that vector particles can be concentrated to a high titre without loss of infectivity (Akkina et al 1996 J. Virol. 70: 2581–5). Retrovirus envelope proteins are apparently unable to withstand the shearing forces during ultracentriftigation, probably because they consist of two non-covalently linked subunits. The interaction between the subunits may be disrupted by the centrifugation. In comparison the VSV glycoprotein is composed of a single unit.

VSV-G protein pseudotyping can therefore offer potential advantages. However, target cell specificities other than those achieved using VSV-G protein may also be desirable. Attempts have been made to alter the target cell range of VSV-G by engineering target sites into the protein. These attempts (Chen et al.) reported at the 1997 meeting on vector targeting strategies for therapeutic gene delivery (Cold Spring Harbor, USA), have not been successful. Other ways of altering retroviral vector target cell range are therefore needed.

Some attempts have been made to efficiently pseudotype retroviruses with other rhabdovirus envelopes. A single report (Reiser et al.), at the 1997 meeting on vector targeting strategies for therapeutic gene delivery (Cold Spring Harbor, USA), claimed that the glycoproteins of rabies virus and Mokola virus could pseudotype HIV-1 particles, but that "the titres obtained were far below the ones obtained with the VSV G protein".

The present invention seeks to overcome these problems by providing a retroviral delivery system that has been phenotyped with a rabies protein, in particular a rabies G protein.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A retroviral vector delivery system capable of transducing target cells, wherein the retroviral vector delivery system comprises a first nucleotide sequence encoding at least part of a rabies G protein or mutant, derivative or fragment thereof; and one or more other nucleotide sequences that ensure transduction of a target neuronal cell by the retroviral vector delivery system; wherein the first nucleotide sequence is heterologous with respect to at least one of the other nucleotide sequences; and wherein the rabies G protein or mutant, variant, or fragment thereof pseudotypes the retroviral vector delivery system whereby the retroviral vector delivery system selectively transduces neuronal cells at a higher transduction efficiency than neuronal cells transduced with a retroviral vector delivery system pseudotyped with a VSV-G protein.

2. The retroviral vector delivery system according to claim 1 wherein the first nucleotide sequence encodes all of a rabies G protein or a mutant, variant, or fragment thereof.

3. The retroviral vector delivery system according to claim 1 wherein at least one of the other nucleotide sequences is from a lentivirus or an oncoretrovirus.

4. The retroviral vector delivery system according to claim 1 wherein the other nucleotide sequences are from a lentivirus or an oncoretrovirus.

5. The retroviral vector delivery system according to claim 1 wherein the other nucleotide sequences are from EIAV.

6. The retroviral vector delivery system according to claim 1 wherein the retroviral vector delivery system comprises at least one nucleotide sequence of interest.

7. A viral particle obtainable from the retroviral vector delivery system according to claim 1.

8. A retroviral vector wherein the retroviral vector is the retroviral vector delivery system according to claim 1 or is obtainable therefrom.

9. An isolated cell transduced with the retroviral vector delivery system according to claim 1, or transduced with a viral particle obtainable therefrom.

10. A pharmaceutical composition comprising the retroviral vector delivery system according to claim 1 and a pharmaceutically acceptable diluent.

11. A method of selectively transducing a neuronal target site comprising contacting a cell with the retroviral vector delivery system of claim 1, or a viral particle obtainable therefrom whereby the neuronal target site is transduced with higher transduction efficiency than a neuronal target site transduced with a retroviral vector delivery system pseudotyped with a VSV-G protein.

12. The retroviral vector delivery system of claim 1, wherein the retroviral delivery system is selected from the group consisting of MLV, HIV and EIAV vectors.

13. The retroviral vector delivery system according to claim 6 wherein the nucleotide sequence of interest is a therapeutic nucleotide of interest or encodes a protein that is a therapeutic protein.

14. A method of selectively delivering a nucleotide sequence of interest to a neuronal target site comprising contacting the retroviral vector delivery system according to claim 6, with said neuronal target site, whereby said neuronal target site is transduced with higher transduction efficiency than a neuronal target site transduced with a retroviral vector delivery system pseudotyped with a VSV-G protein.

15. A method of affecting the infectious profile of a retrovirus or a retroviral vector or a retroviral particle comprising the step of pseudotyping the retrovirus or the retroviral vector or the retroviral particle with a rabies G protein, wherein the pseudotyped retrovirus or the pseudotyped retroviral vector or the pseudotyped retroviral particle selectively transduces target cells with higher transduction efficiencies in neuronal cells than in neuronal cells transduced with a retrovirus or a retroviral vector or a retroviral particle pseudotyped with a VSV-G protein.

16. A method of affecting the host range and/or cell tropism of a retrovirus or a retroviral vector or a retroviral particle comprising the step of pseudotyping the retrovirus or the retroviral vector or the retroviral particle with a rabies G protein, wherein the pseudotyped retrovirus or the pseudotyped retroviral vector or the pseudotyped retroviral particle selectively transduces target cells with higher transduction efficiencies in neuronal cells than in neuronal cells transduced with a retrovirus or a retroviral vector or a retroviral particle pseudotyped with a VSV-G protein.

17. A retrovirus or a retroviral vector or a retroviral particle pseudotyped with a rabies G protein, wherein the retrovirus or the retroviral vector or the retroviral particle selectively transduces target cells with higher transduction efficiencies in neuronal cells than in neuronal cells transduced with a retrovirus or a retroviral vector or a retroviral particle pseudotyped with a VSV-G protein.

18. A retroviral vector delivery system comprising a heterologous env region, wherein the heterolgous env region comprises at least a part of a nucleotide sequence encoding a rabies G protein and wherein the retroviral vector delivery system selectively transduces target cells with higher transduction efficiencies in neuronal cells than in neuronal cells transduced with a retrovirus or a retroviral vector or a retroviral particle pseudotyped with a VSV-G protein.

19. A retroviral vector delivery system comprising a heterolgous env region, wherein the heterolgous env region comprises a nucleotide sequence encoding a rabies G protein and wherein the retroviral vector delivery system selectively transduces target cells with higher transduction efficiencies in neuronal cells than in neuronal cells transduced with a retrovirus or a retroviral vector or a retroviral particle pseudotyped with a VSV-G protein.

20. A retrovirus or retroviral vector or retroviral particle pseudotyped with a rabies G protein, wherein the retrovirus, retroviral vector or retroviral particle selectively transduces target cells with higher transduction efficiencies in neuronal cells than in neuronal cells transduced with a retrovirus or a retroviral vector or a retroviral particle pseudotyped with a VSV-G protein.

21. A method of selectively delivering a nucleotide sequence of interest to a neuronal target site comprising contacting a neuronal target cell with a retroviral vector delivery system pseudotyped with a rabies G protein, mutant, variant, or fragment thereof; wherein said retroviral vector delivery system comprises at least one nucleotide sequence of interest, and wherein said retroviral vector delivery system transduces said neuronal target site with higher transduction efficiency than a neuronal target site transduced with a retoviral vector delivery system pseudotyped with a VSV-G protein.

* * * * *